United States Patent
Tung et al.

(10) Patent No.: US 7,829,748 B1
(45) Date of Patent: *Nov. 9, 2010

(54) PROCESS FOR THE MANUFACTURE OF 1,3,3,3-TETRAFLUOROPROPENE

(75) Inventors: Hsuehsung Tung, Getzville, NY (US); Robert C. Johnson, Lancaster, NY (US); Daniel C. Merkel, Orchard Park, NY (US); Haiyou Wang, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/563,458

(22) Filed: Sep. 21, 2009

(51) Int. Cl.
*C07C 17/00* (2006.01)

(52) U.S. Cl. .................. 570/164; 570/153; 570/158; 570/170

(58) Field of Classification Search .......... 570/164, 570/170
See application file for complete search history.

(56) References Cited

U.S. PATENT DOCUMENTS

| | | | |
|---|---|---|---|
| 5,710,352 A | 1/1998 | Tung | 570/166 |
| 5,895,825 A | 4/1999 | Elsheikh et al. | 570/167 |
| 5,986,151 A | 11/1999 | Van Der Puy | 570/175 |
| 6,124,510 A | 9/2000 | Elsheikh et al. | 570/156 |
| 6,472,573 B1 | 10/2002 | Yamamoto et al. | 570/164 |
| 7,230,146 B2 * | 6/2007 | Merkel et al. | 570/155 |
| 7,592,494 B2 * | 9/2009 | Tung et al. | 570/164 |
| 2003/0060670 A1 | 3/2003 | Van Der Puy et al. | 570/155 |

FOREIGN PATENT DOCUMENTS

| | | |
|---|---|---|
| EP | 0 939 071 A1 | 9/1999 |
| EP | 0974571 | 1/2000 |
| EP | 1067106 | 1/2001 |
| JP | 10007604 | 1/1998 |
| JP | 10007605 | 1/1998 |

* cited by examiner

*Primary Examiner*—Sikarl A Witherspoon
(74) *Attorney, Agent, or Firm*—Bruce O. Bradford

(57) ABSTRACT

The invention provides an economic process for the manufacture of 1,3,3,3-tetrafluoropropene (HFO-1234ze) by a two stage process. A vapor phase hydrofluorination of 1-chloro-3,3,3-trifluoropropene (HCFC-1233zd) into 1-chloro-1,3,3,3-tetrafluoropropane (HCFC-244fa) and/or 1,1,1,3,3-pentafluoropropane (HFC-245fa) is conducted, followed by the thermal dehydrochlorination of HCFC-244fa and dehydrofluorination of HFC-245fa into HFO-1234ze in the presence of a catalyst which comprises one or more of alkali metal halides, alkaline earth metal halides, halogenated metal oxides, zero oxidation state metals, zinc halides, palladium halides, and activated carbon.

20 Claims, No Drawings

PROCESS FOR THE MANUFACTURE OF 1,3,3,3-TETRAFLUOROPROPENE

BACKGROUND OF THE INVENTION

1. Field of the Invention

This invention relates a process for the manufacture of 1,3,3,3-tetrafluoropropene (HFO-1234ze). More particularly, the invention pertains to a process for the manufacture of HFO-1234ze by a two stage process. The process comprises a vapor phase hydrofluorination of 1-chloro-3,3,3-trifluoropropene (HCFC-1233zd) into 1-chloro-1,3,3,3-tetrafluoropropane (HCFC-244fa) and/or 1,1,1,3,3-pentafluoropropane (HFC-245fa), followed by the thermal dehydrochlorination of HCFC-244fa and dehydrofluorination of HFC-245fa in the presence of a catalyst, thus forming a reaction product which comprises 1,3,3,3-tetrafluoropropene.

2. Description of the Related Art

Traditionally, chlorofluorocarbons (CFCs) like trichlorofluoromethane and dichlorodifluoromethane have been used as refrigerants, blowing agents and diluents for gaseous sterilization. In recent years, there has been widespread concern that certain chlorofluorocarbons might be detrimental to the Earth's ozone layer. As a result, there is a worldwide effort to use halocarbons which contain fewer or no chlorine substituents. Accordingly, the production of hydrofluorocarbons, or compounds containing only carbon, hydrogen and fluorine, has been the subject of increasing interest to provide environmentally desirable products for use as solvents, blowing agents, refrigerants, cleaning agents, aerosol propellants, heat transfer media, dielectrics, fire extinguishing compositions and power cycle working fluids. In this regard, 1,3,3,3-tetrafluoropropene (HFO-1234ze) is a compound that has the potential to be used as a zero Ozone Depletion Potential (ODP) and a low Global Warming Potential (GWP) refrigerant, blowing agent, aerosol propellant, solvent, etc, and also as a fluorinated monomer.

It is known in the art to produce HFO-1234ze. For example, U.S. Pat. No. 5,710,352 teaches the fluorination of 1,1,1,3,3-pentachloropropane (HCC-240fa) to form HCFC-1233zd and a small amount of HFO-1234ze. U.S. Pat. No. 5,895,825 teaches the fluorination of HCFC-1233zd to form HFO-1234ze. U.S. Pat. No. 6,472,573 also teaches the fluorination of HCFC-1233zd to form HFO-1234ze. U.S. Pat. No. 6,124,510 teaches the formation of cis and trans isomers of HFO-1234ze by the dehydrofluorination of HFC-245fa using either a strong base or a chromium-based catalyst. Additionally, European patent EP 0939071 describes the formation of HFC-245fa via the fluorination of HCC-240fa through intermediate reaction product which is an azeotropic mixture of HCFC-1233zd and HFO-1234ze.

It has been determined that these known processes are not economical relative to their product yield. Accordingly, the present invention provides an alternate process for forming HFO-1234ze which is more economical than prior art processes and at a higher yield as compared to known processes. In particular, it has now been found that HFO-1234ze may be formed by a two step reaction involving the hydrofluorination of 1-chloro-3,3,3-trifluoropropene (HCFC-1233zd) into 1-chloro-1,3,3,3-tetrafluoropropane (HCFC-244fa) and optionally 1,1,1,3,3-pentafluoropropane (HFC-245fa), followed by the dehydrochlorination of HCFC-244fa and dehydrofluorination of HFC-245fa via thermal decomposition in the presence of a catalyst.

SUMMARY OF THE INVENTION

The invention also provides a process for the manufacture of 1,3,3,3-tetrafluoropropene comprising:

a) reacting 1-chloro-3,3,3-trifluoropropene with hydrogen fluoride in a reactor in the vapor phase and in the presence of a fluorination catalyst and under conditions sufficient to form an intermediate product which comprises 1-chloro-1,3,3,3-tetrafluoropropane and/or 1,1,1,3,3-pentafluoropropane; and b) thermally decomposing the intermediate product in the presence of a catalyst which comprises one or more of alkali metal halides, alkaline earth metal halides, halogenated metal oxides, zero oxidation state metals, zinc halides, palladium halides, cerium halides, yttrium halides, aluminum halides, and activated carbon, under conditions sufficient to dehydrochlorinate 1-chloro-1,3,3,3-tetrafluoropropane and/or to dehydrofluorinate 1,1,1,3,3-pentafluoropropane, forming 1,3,3,3-tetrafluoropropene.

DESCRIPTION OF THE INVENTION

The first step (a) of the process of the invention involves the formation of 1-chloro-1,3,3,3-tetrafluoropropane (HCFC-244fa) and/or 1,1,1,3,3-pentafluoropropane (HFC-245fa) by reacting 1-chloro-3,3,3-trifluoropropene (HCFC-1233zd) with hydrogen fluoride (HF) in the vapor phase, in the presence of a fluorination catalyst. This reaction proceeds as follows:

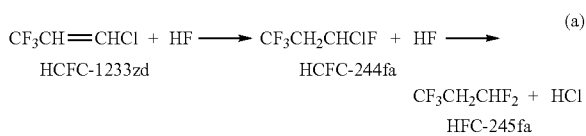

(a)

The result is a reaction mixture comprising one or both of the two intermediate reaction products, HCFC-244fa and HFC-245fa. In the preferred embodiment of the invention, the mole ratio of HF to HCFC-1233zd for this reaction preferably ranges from about 1:1 to about 50:1, more preferably from about 2:1 to about 30:1 and most preferably from about 3:1 to about 20:1.

The 1-chloro-3,3,3-trifluoropropene (HCFC-1233zd) employed may be either solely the trans isomer form, or solely the cis isomer form or a combination of both the trans and cis isomers forms. In one embodiment, the HCFC-1233zd comprises from about 60% to about 100% of the trans isomer form with the balance being the cis isomer form. In another embodiment, the HCFC-1233zd comprises from about 70% to about 100% of the trans isomer form with the balance being the cis isomer form. In yet another embodiment, the HCFC-1233zd comprises from about 80% to about 100% of the trans isomer form with the balance being the cis isomer form.

Preferred fluorination catalysts include, but are not limited to, transition metal halides, Group IVb and Vb metal halides, and combinations thereof, preferably supported on activated carbon or fluorinated alumina. More specifically, preferred fluorination catalysts non-exclusively include $SbCl_5$, $SbCl_3$, $TaCl_5$, $SnCl_4$, $NbCl_5$, $TiCl_4$, $MoCl_5$, $Cr_2O_3/Al_2O_3$, $Cr_2O_3/AlF_3$, $Cr_2O_3/carbon$, $COCl_2/Cr_2O_3/Al_2O_3$, $NiCl_2/Cr_2O_3/Al_2O_3$, $COCl_2/AlF_3$, $NiCl_2/AlF_3$ and mixtures thereof, where it is understood that after pre-treatment with HF or during reaction in the presence of HF the above mentioned catalyst will be partially fluorinated. The preferred catalysts are $SbCl_3$ and $SbCl_5$ halides supported on activated carbon.

Fluorination catalysts having a purity of at least 98% are preferred. The fluorination catalyst is present in an amount sufficient to drive the reaction. The fluorination reaction may be conducted in any suitable fluorination reaction vessel or reactor but it should preferably be constructed from materials which are resistant to the corrosive effects of hydrogen fluoride such as nickel and its alloys, including Hastelloy, Inconel, Incoloy, and Monel or vessels lined with fluoropolymers.

Any water in the hydrogen fluoride (HF) will react with and deactivate the fluorination catalyst. Therefore substantially anhydrous hydrogen fluoride is preferred. By "substantially anhydrous" it is meant that the HF contains less than about 0.05 weight % water and preferably contains less than about 0.02 weight % water. However, one of ordinary skill in the art will appreciate that the presence of water in the HF can be compensated for by increasing the amount of catalyst used.

The reaction of step (a) is preferably conducted at a temperature of from about 50° C. to about and 200° C., more preferably from about 60° C. to about 180° C. and most preferably from about 65° C. and 150° C. Step (a) is also preferably conducted at a pressure of from about 15 psia to about 215 psia, more preferably from about 15 psia to about 165 psia and most preferably from about 30 psia to about 100 psia. In the process of the invention, the reactor is preferably preheated to the desired fluorination reaction temperature while anhydrous HF is fed to the reactor. The HCFC-1233zd and HF may be fed to the reactor at the desired temperatures and pressures that are described herein. In a preferred embodiment of the invention, either or both of the HCFC-1233zd and HF are pre-vaporized or preheated prior to entering the reactor. Alternately, the HCFC-1233zd and HF are vaporized inside the reactor. During the fluorination reaction, HCFC-1233zd and HF are reacted in a vapor phase with the fluorination catalyst. The reactant vapor is allowed to contact the fluorination catalyst for from about 0.01 to about 240 seconds, more preferably from about 0.1 to about 60 seconds and most preferably from about 0.5 to about 20 seconds.

In the preferred embodiment, the process flow of step (a) is in the down direction through a bed of the catalyst. Before each use, the catalyst is preferably dried, pre-treated and activated. It may also be advantageous to periodically regenerate the catalyst after prolonged use while in place in the reactor. For $Cr_2O_3$, $Cr_2O_3/Al_2O_3$, $Cr_2O_3/AlF_3$, $Cr_2O_3$/carbon, $COCl_2/Cr_2O_3/Al_2O_3$, $NiCl_2/Cr_2O_3/Al_2O_3$, $COCl_2/AlF_3$, $NiCl_2/AlF_3$ catalysts, pre-treatment can be done by heating the catalyst to about 250° C. to about 430° C. in a stream of nitrogen or other inert gas. The catalyst may then be activated by treating it with a stream of HF diluted with a large excess of nitrogen gas in order to obtain high catalyst activity. Regeneration of the catalyst may be accomplished by any means known in the art such as, for example, by passing air or air diluted with nitrogen over the catalyst at temperatures of from about 100° C. to about 400° C., preferably from about 200° C. to about 375° C., for from about 1 hour to about 3 days, depending on the size of the reactor. For $SbCl_5$, $SbCl_3$, $TaCl_5$, $SnCl_4$, $NbCl_5$, $TiCl_4$, $MoCl_5$ catalysts, supported on a solid support such as activated carbon, pre-treatment or activation can be done by first heating the catalyst to about 30° C. to 250° C. in a stream of nitrogen or other inert gas. It is then treated with a stream of HF in the absence or presence of an oxidizing agent such as chlorine gas in order to obtain high catalyst activity. In addition, the catalyst may optionally be kept active by co-feeding chlorine to the reactor during reaction.

HCFC-244fa and HFC-245fa may be recovered from the fluorination reaction product mixture comprised of unreacted starting materials and by-products, including HCl, by any means known in the art, such as by extraction and preferably distillation. For example, the distillation may be preferably conducted in a standard distillation column at a pressure which is less than about 300 psig, preferably less than about 150 psig and most preferably less than 100 psig. The pressure of the distillation column inherently determines the distillation operating temperature. HCl may be recovered by operating the distillation column at from about −40° C. to about 25° C., preferably from about −40° C. to about −20° C. Single or multiple distillation columns may be used. The distillate portion includes substantially all the HCFC-244fa, HFC-245fa, unreacted HF and HCl produced in the reaction as well as any other impurities. In the preferred embodiment, HCFC-244fa and the HFC-245fa are separated from all other reaction by-products and unreacted HF for further reaction in step (b) described herein. In the preferred embodiment, any HF present may also be recovered and recycled back for subsequent fluorination reactions.

Once reaction step (a) is completed, the second step (b) is the conversion of the reaction mixture obtained from (a), which contains substantially HCFC-244fa and/or HFC-245fa, to HFO-1234ze. As the reaction formulas below illustrate, HFO-1234ze is formed by the dehydrochlorination of HCFC-244fa and the dehydrofluorination of HFC-245fa. In the preferred embodiment of the invention, the dehydrochlorination of HCFC-244fa and dehydrofluorination of HFC-245fa are accomplished by reacting at an elevated temperature by thermal decomposition in the presence of a catalyst. The preferred temperatures for the thermal decomposition are from about 30° C. to about 550° C., more preferably from about 300° C. to about 550° C. As above, the reaction is preferably conducted at atmospheric pressure, super-atmospheric pressure or under vacuum. The vacuum pressure can be from about 5 ton to about 760 torr.

The reaction for the dehydrochlorination of HCFC-244fa and dehydrofluorination of HFC-245fa is conducted in the presence of a catalyst. Preferred catalyst in step (b) comprises one or more of supported or bulk metals of Pd, Pt, Rh, Fe, Co, Ni, Cu, Mo, Cr, Mn, magnesium halides, calcium halides, lithium halides, sodium halides, potassium halides, cesium halides, cerium halides, yttrium halides, aluminum halides, halogenated magnesium oxides, halogenated calcium oxides, halogenated barium oxides, halogenated zinc oxides, halogenated cesium oxides, halogenated aluminum oxides, and combinations thereof.

More preferred catalyst in step (b) comprises one or more of supported or bulk MgO, CaO, BaO, ZnO, CsO, $Al_2O_3$, LiF, NaF, KF, CsF, $MgF_2$, $CaF_2$, LiCl, NaCl, KCl, $CeF_4$, $FeF_3$, $YF_3$, $AlF_3$ and CsCl, Most preferred catalyst in step (b) comprises a combination of CsCl and MgO, or a combination of CsCl and $MgF_2$.

Preferably, the reactor effluent is fed to a caustic scrubber or to a distillation column to remove the by-product of HCl to produce an acid-free organic product which, optionally, may undergo further purification.

The reactions of both step (a) and step (b) may be conducted in any suitable reactor. Further, the dehydrochlorination of 1-chloro-1,3,3,3-tetrafluoropropane (HCFC-244fa) and the dehydrofluorination of 1,1,1,3,3-pentafluoropropane (HFC-245fa) may either be conducted simultaneously in the same reactor, or they may first be separated followed by separately dehydrochlorinating 1-chloro-1,3,3,3-tetrafluoropropane by thermal decomposition and separately dehydrofluorinating 1,1,1,3,3-pentafluoropropane by thermal decomposition. The result of this two step process is a high yield of HFO-1234ze.

The following non-limiting examples serve to illustrate the invention.

Examples 1-18

A fluorination reaction was conducted in a 2.54 cm diameter, 81 cm long Monel® reactor. The reactor was heated with an electric furnace. The reactants of HCFC-1233zd (>99.9% purity), anhydrous HF and, optionally, chlorine, were fed to the reactor at constant flow rates. The flow rate of the chlorine was measured using a Hasting mass flow meter and controller. The flow rate for the reactants, HCFC-1233zd and HF, were controlled and measured by Honeywell PlantScape DCS (Distributive Control System) and confirmed by the weight change in the respective source cylinders.

The reactor output was sampled directly into an in-line GC, i.e. a Perkin Elmer 8500 gas chromatograph, using a Fluorocol column and FID detector, so that the amounts of organic species exiting the reactor could be determined during the operation of the process.

The reaction conditions for Examples 1-18 and corresponding experimental results are listed below in Tables 1 and 2, respectively. Contact time is defined as bulk volume (in ml) of catalyst divided by volumetric flow rate of reactants (in ml/sec).

Preparation of catalyst 1 and 2 are described below:

Catalyst 1

This catalyst was made by impregnating $SbCl_5$ (250 g) on granular Shiro Sagi G2X (4×6 mesh) activated carbon (500 ml). It was charged to the reactor and activated in the reactor before use. Activation procedures were as follows: at first, nitrogen of 20 ml/min was flowed over the catalyst. In this nitrogen atmosphere, the reactor was heated to 100° C. Then, anhydrous HF and chlorine were allowed to flow through the reactor at 0.25 g/min and 0.3 g/min, respectively, for 30 minutes to 1 hour, depending on volume of catalyst. Once the activation is complete, the HF and chlorine flows were stopped and the catalyst was cooled to the desired reaction temperature under a nitrogen atmosphere.

Catalyst 2

This catalyst was made and activated using the same procedures as those for catalyst 1, except that Toyo Calgon PCB (4×10 mesh) activated carbon was used instead. The amounts of $SbCl_5$ and activated carbon used were 169 g and 340 ml, respectively.

Reaction Conditions

| Example # | Catalyst | Pressure (psia) | Temp. ° C. | Contact Time (sec) | $Cl_2$/org mole ratio | HF/org mole ratio |
|---|---|---|---|---|---|---|
| 1 | 1 | 15 | 80 | 4.6 | 0.0 | 10 |
| 2 | 1 | 15 | 80 | 8.9 | 0.0 | 10 |
| 3 | 1 | 15 | 80 | 27.4 | 0.0 | 10 |
| 4 | 2 | 15 | 80 | 0.9 | 0.0 | 10 |
| 5 | 2 | 15 | 80 | 1.9 | 0.0 | 10 |
| 6 | 2 | 15 | 80 | 6.3 | 0.0 | 10 |
| 7 | 2 | 30 | 65 | 1.1 | 0.015 | 10 |
| 8 | 2 | 30 | 65 | 2 | 0.015 | 10 |
| 9 | 2 | 30 | 65 | 10.1 | 0.015 | 10 |
| 10 | 2 | 30 | 85 | 1 | 0.015 | 10 |
| 11 | 2 | 30 | 85 | 1.9 | 0.015 | 10 |
| 12 | 2 | 30 | 85 | 9.5 | 0.015 | 10 |
| 13 | 2 | 60 | 85 | 2 | 0.015 | 10 |
| 14 | 2 | 60 | 85 | 5.2 | 0.015 | 10 |
| 15 | 2 | 60 | 85 | 10.4 | 0.015 | 10 |
| 16 | 1 | 45 | 70 | 1.5 | 0.015 | 10 |
| 17 | 1 | 45 | 70 | 2.5 | 0.015 | 10 |
| 18 | 1 | 45 | 70 | 11.5 | 0.015 | 10 |

Experimental Results

| Example # | HFO-1234ze | HFC-245fa | HCFC-1233zd | HCFC-244fa | Others |
|---|---|---|---|---|---|
| 1 | 0.02 | 77.31 | 7.82 | 13.28 | 1.57 |
| 2 | 0.01 | 91.90 | 2.32 | 5.16 | 0.61 |
| 3 | 0.00 | 99.11 | 0.07 | 0.39 | 0.43 |
| 4 | 0.21 | 20.66 | 62.79 | 15.71 | 0.64 |
| 5 | 0.34 | 50.08 | 27.90 | 20.76 | 0.93 |
| 6 | 0.09 | 90.41 | 4.26 | 4.14 | 1.10 |
| 7 | 0.13 | 38.19 | 32.76 | 27.69 | 1.23 |
| 8 | 0.03 | 39.68 | 26.12 | 32.62 | 1.54 |
| 9 | 0.01 | 70.83 | 4.64 | 22.28 | 2.24 |
| 10 | 0.16 | 55.03 | 26.40 | 17.14 | 1.28 |
| 11 | 0.05 | 64.26 | 14.90 | 19.12 | 1.66 |
| 12 | 0.00 | 91.67 | 2.01 | 5.30 | 1.02 |
| 13 | 0.13 | 14.86 | 57.38 | 25.05 | 1.56 |
| 14 | 0.05 | 43.94 | 24.95 | 28.09 | 2.44 |
| 15 | 0.07 | 42.29 | 22.82 | 30.22 | 3.69 |
| 16 | 0.10 | 22.14 | 50.61 | 25.95 | 1.19 |
| 17 | 0.16 | 34.85 | 35.99 | 27.65 | 1.35 |
| 18 | 0.04 | 92.97 | 0.99 | 5.30 | 0.71 |

The results showed that the shorter the contact time the more HCFC-244fa was formed, indicating that 244fa is an intermediate from the reaction of HFC-1233zd with HF to make HFC-245fa. Process conditions using shorter contact time are preferred, because HFO-1234ze made from HCFC-244fa is cheaper and easier than that from HFC-245fa. The unreacted 1233zd and HF can be recycled back to the reactor to make more HCFC-244fa and HFC-245fa.

Example 19

This example illustrates the continuous vapor phase dehydrochlorination reaction of 1-chloro-1,3,3,3-tetrafluoropropane (HCFC-244fa)→1,3,3,3-tetrafluoropropene (HFO-1234ze)+HCl. The dehydrochlorination catalyst for the experiment is 10 wt % CsCl/90 wt % $MgF_2$.

Conversion of HCFC-244fa into HFO-1234ze is performed using a Monel reactor (ID 2 inches, length 32 inches) equipped with a Monel preheater (ID 1 inch, length 32 inches) which is filled with Nickel mesh to enhance heat transfer. The reactor is filled with 2.0 liters of pelletized 10 wt % CsCl/90 wt % $MgF_2$ dehydrochlorination catalyst. Nickel mesh is placed at the top and at the bottom of reactor to support the catalyst. A multi-point thermocouple is inserted at the center of the reactor to monitor the catalyst bed temperature. The catalyst is pretreated in dry $N_2$ flow for 6 hours at the temperature of 480° C. Then the feed with the composition 98.0 GC % HCFC-244bb/0.9 GC % HCFO-1233zd/1.1 GC % HFC-245fa is introduced into the reactor at the rate of 1.0 lb/hr. The feed is vaporized prior to entering the reactor preheater. The feed rate is maintained constant at 1.0 lbs/hr and both temperature and pressure are varied. The productivity range of the catalyst is estimated at 3-6 lbs/hr/ft$^3$. The highest productivity is observed at 470° C. and 45 psig, and the lowest productivity is observed at 480° C. and 3 psig. The reaction products are passed through a caustic scrubber to remove HCl by-product. Then the product stream is passed through a column filled with desiccant to remove residual moisture and collected in a cold trap.

Reaction Data

480° C. at 3 psig—HCFC-244fa conversion ~30%, Selectivity to HFO-1234ze ~97%

480° C. at 20 psig—HCFC-244fa conversion ~47%, Selectivity to HFO-1234ze ~96%

470° C. at 20 psig—HCFC-244fa conversion ~36%, Selectivity to HFO-1234ze ~97%

470° C. at 45 psig—HCFC-244fa conversion ~53%, Selectivity to HFO-1234ze ~96%

460° C. at 45 psig—HCFC-244fa conversion ~38%, Selectivity to HFO-1234ze ~99%

Example 20

In a typical experiment, a 2.54 cm×81 cm Monel® reactor is used. About 500 ml of catalyst supported on activated carbon is packed into the reactor. The reactor is heated to 150° C. under 1 liter/hr of nitrogen flow to dry the catalyst for 4 hours. Then, the reactor temperature is brought to 250° C. under the same nitrogen flow and HCFC-244fa is fed to the reactor at 1 g/min, and in the mean time the nitrogen flow is stopped. HFO-1234ze is found by using the in-line GC at the outlet of the reactor at 98% selectivity and 95% single pass conversion.

Example 21

The same experiment described in Example 20 is repeated, except that HFC-245fa is used as feed. At the outlet of the reactor, HFO-1234ze is found at 95% selectivity and 85% single pass conversion.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A process for the manufacture of 1,3,3,3-tetrafluoropropene comprising:
   a) reacting 1-chloro-3,3,3-trifluoropropene with hydrogen fluoride in a reactor in the vapor phase and in the presence of a fluorination catalyst and under conditions sufficient to form an intermediate product which comprises 1-chloro-1,3,3,3-tetrafluoropropane and/or 1,1,1,3,3-pentafluoropropane; and
   b) thermally decomposing the intermediate product in the presence of a catalyst which comprises one or more of alkali metal halides, alkaline earth metal halides, halogenated metal oxides, zero oxidation state metals, zinc halides, palladium halides, cerium halides, yttrium halides, aluminum halides, and activated carbon, under conditions sufficient to dehydrochlorinate 1-chloro-1,3,3,3-tetrafluoropropane and/or to dehydrofluorinate 1,1,1,3,3-pentafluoropropane, forming 1,3,3,3-tetrafluoropropene.

2. The process of claim 1 wherein the intermediate product comprises 1-chloro-1,3,3,3-tetrafluoropropane.

3. The process of claim 1 wherein the intermediate product comprises 1,1,1,3,3-pentafluoropropane.

4. The process of claim 1 wherein the intermediate product comprises both 1-chloro-1,3,3,3-tetrafluoropropane and 1,1,1,3,3-pentafluoropropane.

5. The process of claim 1 which comprises reacting the trans isomer form of 1-chloro-3,3,3-trifluoropropene.

6. The process of claim 1 which comprises reacting the cis isomer form of 1-chloro-3,3,3-trifluoropropene.

7. The process of claim 1 which comprises reacting both the trans and cis isomer forms of 1-chloro-3,3,3-trifluoropropene.

8. The process of claim 1 wherein the dehydrochlorination of 1-chloro-1,3,3,3-tetrafluoropropane and the dehydro fluorination of 1,1,1,3,3-pentafluoro-propane are conducted simultaneously in the same reactor.

9. The process of claim 1 wherein step (a) is conducted at a temperature of from about 50° C. to about and 200° C.

10. The process of claim 1 wherein step (a) is conducted at a pressure of from about 15 psia to about 215 psia.

11. The process of claim 1 wherein in step (a) 1-chloro-3,3,3-trifluoropropene vapor and hydrogen fluoride vapor contact the fluorination catalyst for from about 0.01 to about 240 seconds.

12. The process of claim 1 wherein step (b) is conducted by first separating 1-chloro-1,3,3,3-tetrafluoropropane and 1,1,1,3,3-pentafluoropropane, and then separately dehydrochlorinating 1-chloro-1,3,3,3-tetrafluoropropane and separately dehydrofluorinating 1,1,1,3,3-pentafluoropropane.

13. The process of claim 1 wherein the fluorination catalyst is selected from the group consisting of transition metal halides, Group IVb metal halides, Group Vb metal halides and combinations thereof on activated carbon or fluorinated alumina.

14. The process of claim 1 wherein the catalyst in step (b) comprises one or more of supported or bulk metals, magnesium halides, calcium halides, lithium halides, sodium halides, potassium halides, cesium halides, cerium halides, yttrium halides, aluminum halides, halogenated magnesium oxides, halogenated calcium oxides, halogenated barium oxides, halogenated zinc oxides, halogenated cesium oxides halogenated aluminum oxides, and combinations thereof.

15. The process of claim 1 wherein the catalyst in step (b) comprises one or more of supported or bulk LiF, NaF, KF, CsF, MgF$_2$, CaF$_2$, LiCl, NaCl, KCl, CeF$_4$, FeF$_3$, YF$_3$, AlF$_3$, CsCl, MgO, CaO, BaO, ZnO, CsO, Al$_2$O$_3$, Pd, Pt, Rh, Fe, Co, Ni, Cu, Mo, Cr, and Mn.

16. The process of claim 1 wherein the catalyst in step (b) comprises a combination of CsCl and MgO, or a combination of CsCl and MgF$_2$.

17. The process of claim 16 wherein the catalyst in step (b) comprises from 5 to 25 wt % CsCl.

18. The process of claim 1 wherein the temperature for the thermal decomposition ranges from about 30° C. to about 550° C.

19. The process of claim 1 wherein the temperature for the thermal decomposition ranges from about 300° C. to about 550° C.

20. The process of claim 1 wherein the pressure for the thermal decomposition ranges from about 5 ton to about 760 torr.

* * * * *